United States Patent [19]

Wang et al.

[11] Patent Number: 4,925,785
[45] Date of Patent: May 15, 1990

[54] NUCLEIC ACID HYBRIDIZATION ASSAYS

[75] Inventors: Chang-Ning J. Wang, Chelmsford; Lynn C. Klotz, Cambridge, both of Mass.

[73] Assignee: Biotechnica Diagnostics, Inc., Cambridge, Mass.

[21] Appl. No.: 837,701

[22] Filed: Mar. 7, 1986

[51] Int. Cl.$^5$ .............................................. C12Q 1/68
[52] U.S. Cl. ...................................... 435/6; 435/803; 436/501; 935/78
[58] Field of Search ...................... 435/, 803; 436/501; 935/78

[56] References Cited

U.S. PATENT DOCUMENTS

| | | |
|---|---|---|
| 4,166,105 | 8/1979 | Hirschfeld . |
| 4,358,535 | 11/1982 | Falkow et al. . |
| 4,486,539 | 12/1984 | Ranki et al. . |
| 4,563,417 | 1/1986 | Albarella et al. . |
| 4,576,912 | 3/1986 | Yaverbaum et al. . |
| 4,672,040 | 6/1987 | Josephson ................... 935/77 X |
| 4,716,106 | 12/1987 | Chiswell ..................... 935/78 X |
| 4,749,647 | 6/1988 | Thomas et al. ............... 935/78 X |
| 4,751,177 | 6/1988 | Stabinsky .................... 935/78 X |
| 4,775,619 | 10/1988 | Urdea et al. ................. 435/803 X |
| 4,777,129 | 10/1988 | Dattagupta et al. .......... 935/78 X |
| 4,797,355 | 1/1989 | Stabinsky ..................... 935/78 |

FOREIGN PATENT DOCUMENTS

| | | |
|---|---|---|
| 0128332 | 12/1984 | European Pat. Off. . |
| 0138357 | 4/1985 | European Pat. Off. . |
| 0139489 | 5/1985 | European Pat. Off. . |
| 0147665 | 7/1985 | European Pat. Off. . |
| 0153873 | 9/1985 | European Pat. Off. . |
| 0154505 | 9/1985 | European Pat. Off. . |
| 0154884 | 9/1985 | European Pat. Off. . |
| 0172153 | 2/1986 | European Pat. Off. . |
| 0192168 | 8/1986 | European Pat. Off. . |
| 2156074 | 10/1985 | United Kingdom . |
| WO84/03520 | 9/1984 | World Int. Prop. O. . |

OTHER PUBLICATIONS

Meinkoth et al., 138, Analytic. Biochem., 267 (1984).
Maniatis et al., Molecular Cloning-A Laboratory Manual, 312-361 (1982), Cold Spring Harbor Labs. L.S.H.
Alwine et al., 74, Proc. Natl. Acad. Sci. USA, 5350 (1977).
Grunstein et al., 72, Proc. Natl. Acad. Sci., 3961 (1975).

Primary Examiner—Amelia Burgess Yarbrough
Attorney, Agent, or Firm—Fish & Richardson

[57] ABSTRACT

A method for carrying out a nucleic acid hybridization test to detect a target nucleic acid sequence, the method including the steps of (1) providing a polymer molecule bonded to a first single-stranded nucleic acid sequence which is either (a) a first probe capable of hybridizing to the target nucleic acid sequence, or (b) a second nucleic acid sequence capable of hybridizing to a third nucleic acid sequence bonded to a first probe capable of hybridizing to the target nucleic acid sequence; provided that, where the polymer molecule comprises DNA, the DNA is of heterogeneous base sequence;

(2) where the polymer used in step (1) is bonded to (b), providing the first probe bonded to the third nucleic acid sequence;

(3) denaturing the target nucleic acid sequence;

(4) contacting the denatured target nucleic acid sequence with the polymer molecule bonded to the first single-stranded nucleic acid sequence and, if the first nucleic acid sequence is (b), to the first probe bonded to the third nucleic acid sequence; and (5) detecting complexes between the target nucleic acid sequence and the polymer molecule.

35 Claims, 13 Drawing Sheets

  
FIG.1a     FIG.1b     FIG.1c
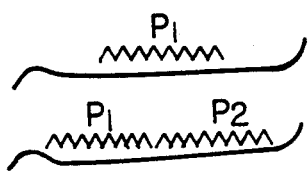 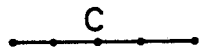 
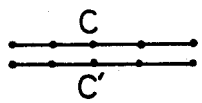
FIG.1d     FIG.1e     FIG.1f
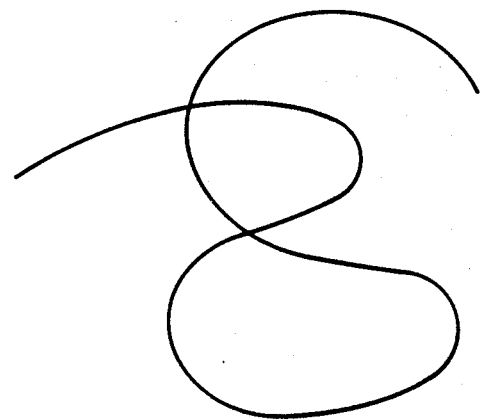 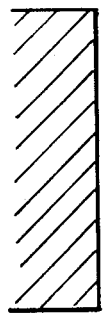
FIG.1g     FIG.1h

NUCLEIC ACID HYBRIDIZATION ASSAYS

BACKGROUND OF THE INVENTION

This invention relates to nucleic acid hybridization methods.

Nucleic acid hybridization using nitrocellulose filters and other planar, solid supports is used to identify specific DNA or RNA sequences. Colony hybridizations in which colonies of organisms are transferred from a culture plate to nitrocellulose filters have been used to identify bacteria, bacteriophages, other organisms, genes within organisms, RNA transcriptional products, recombinant DNA clones, etc. The colony hybridization method from which many frequently used procedures are derived is that of Grunstein and Hogness, 72 Proc. Natl. Acad. Sci. 3961 (1975). A review of the use of nucleic acid filter hybridization procedures in modern molecular biology research is given in Maniatis et al., Molecular Cloning - A Laboratory Manual 312–61 (Cold Spring Harbor Laboratory, New York 1982). A review of nucleic acid filter hybridizations in medical diagnostics is given in Meinkoth et al., 138 Analytic Biochem. 267–84 (1984).

While the standard filter hydridization procedure as practiced by Grunstein and Hogness and many others does provide a sensitive and very specific method for identifying living microorganisms, it does have drawbacks which make it difficult to use routinely in medical clinical reference laboratories or physicians' offices. In order to illustrate the difficulties, the outline below of the steps in a typical standard procedure will be useful:

1. Cells from the sample to be diagnosed are adsorbed onto the nitrocellulose filter where the hybridization is to be carried out.
2. Cells are lysed on the filter and the DNA is denatured and fixed to the filter.
3. Under renaturing conditions, the filter is exposed to labelled probe DNA. If the sample contains DNA sequences complementary to those of the probe DNA, the probe DNA will combine with the sample DNA and thereby bind to the filter, which is then washed to remove uncombined DNA.
4. The filter is then analyzed for binding of probe DNA by detecting the label on the probe DNA. In most research applications the label is P-32, and it is detected using autoradiography by overlaying the filter with P-32 sensitive film and observing dark spots on the film where the P-32 label has hybridized to the sample DNA.

While this procedure is adequate for research use, it requires considerable skill to carry out and is time consuming. For example, the user must typically carry out a many-step procedure just to adsorb the samples on the filter, to lyse the cells, and to fix the sample DNA on the filter (see Alwine et al, 74 Proc. Natl. Acad. Sci., U.S.A., 5350–56 (1977)). In addition, other steps, including many washings, are required to renature the target DNA in the sample with the labelled probe and to wash away all the unreacted probe.

Fairly expensive specialized equipment and many user steps are involved in detecting the P-32 label by autoradiography. Employing P-32 label limits the use of the test because most physicians and many clinical reference laboratory personnel are not trained in or licensed for the use of this radioactive isotope. In addition, radioactive isotopes can be dangerous to the user and are not easily disposed of.

Besides the several user steps required to spot several samples on a filter, having the user spot the samples can lead to unwanted variability in the test. Amounts of sample spotted and the location of the spot on the filter can be variable. This can lead to difficulty in quantitating final results and in automating the procedures, since most automation procedures would require a precise location of the spots on the planar filter.

Some of the difficulties of the typical standard hybridization procedure can be overcome by using the so-called sandwich hybridization procedures. Typically, such procedures utilize two DNA or RNA probe molecules whose base sequences are complementary to the base sequences of adjacent segments of the target DNA or RNA of the organism to be detected. By using two probes the target DNA becomes divalent, analogous to typical antibody molecules. Thus, many diagnostic kit configurations which have been developed based on the divalency of antibodies are then theoretically adaptable to nucleic acid hybridizations. In such test configurations, the target DNA is "sandwiched" between the two probe molecules. Furthermore, the unique properties of nucleic acids allow for test configurations not possible with antibodies.

In addition to the divalency conferred upon the target DNA in sandwich hybridizations, other advantages result. For example, one of the probes ($P_1$), can be bound to the planar filters by the manufacturer of the diagnostic kit. Thus, location of the spot on the filter, the area which the spot covers, and the amount of probe bound to the spot can be carefully controlled by the manufacturer to help eliminate variability in the test results and to aid in automating the tests. The precise spotting of $P_1$ on the filter then directs precisely the target DNA carrying a labelled $P_2$ probe DNA to the filter spot. Furthermore, the manufacturer has carried out many of the user's steps, making the test easier to use.

Sandwich hybridizations, however, do appear to have at least one major disadvantage. In order for the labelled $P_2$ probe to bind to the filter, two reactions must take place: the reaction of probe $P_1$ with target DNA and the reaction of the target DNA with the probe $P_2$. The necessity of two reactions can slow nucleic acid hybridizations considerably, and any method developed to increase significantly the rate of reaction must apply to both reactions, since the overall rate of reaction is approximately the rate of the slowest of the two reaction steps. This is the well-known "bottleneck" principle of chemical kinetics.

In molecular biology research, nucleic acid hybridizations utilizing sandwiches as described above were first described by Dunn and Hassell, 12 Cell 23 (1977), where a sandwich method was used to detect viral nucleic acid sequences.

Sandwich hybridization tests utilizing radioactive labels have been used to detect viral and bacterial genes are described in Ranki et al., U.S. Pat. No. 4,563,419, and Ranki et al. U.S. Pat. No. 4,486,539, which are hereby incorporated by reference.

SUMMARY OF THE INVENTION

In general, the invention features a method for carrying out a nucleic acid hybridization test to detect a target nucleic acid sequence by the steps of:

(1) providing a polymer molecule bonded to a first single-stranded nucleic acid sequence which is either (a) a first probe capable of hybridizing to the target nucleic acid sequence, or (b) a second nucleic acid sequence capable of hybridizing to a third nucleic acid sequence bonded to a first probe capable of hybridizing to the target nucleic acid sequence, provided that where the polymer is DNA, the DNA is of heterogeneous base sequence;

(2) where the polymer used in step (1) is bonded to (b), providing the first probe bonded to the third nucleic acid sequence;

(3) denaturing the target nucleic acid sequence;

(4) contacting the denatured target nucleic acid sequence with the polymer molecule bonded to the first single-stranded nucleic acid sequence and, if the first nucleic acid sequence is (b), to the first probe bonded to the third nucleic acid sequence; and (5) detecting complexes between the target nucleic acid sequence and the polymer molecule.

In some preferred embodiments, the polymer has one or more labels attached. One such embodiment further includes the steps of:

(6) providing a solid support bonded to a plurality of a fourth single-stranded nucleic acid sequence which is either (c) a second single-stranded nucleic acid probe sequence capable of hybridizing to the target nucleic acid sequence, or (d) a nucleic acid sequence capable of hybridizing to a fifth nucleic acid sequence that is bonded to either (i) the first probe, or (ii) a second probe;

(7) where the fourth nucleic acid sequence in step (6) is a nucleic acid sequence capable of hybridizing to a fifth nucleic acid sequence bonded to the first probe, providing the first probe sequence bonded both to the third nucleic acid sequence and the fifth nucleic acid sequence; and (8) where the fourth nucleic acid sequence in step (6) is a nucleic acid sequence capable of hybridizing to a fifth nucleic acid sequence bonded to a second probe, providing the second probe sequence bonded to the fifth nucleic acid sequence; and wherein step (4) further comprises contacting the denatured target nucleic acid sequence with the solid support bonded to the fourth nucleic acid sequence and, if that sequence is (d), either the first probe, where the fifth nucleic acid sequence is bonded to (i), or the second probe, where the fifth nucleic acid sequence is bonded to (ii).

Step (5) preferably involves determining the amount of label bound to the solid support, and the fourth single-stranded nucleic acid sequence is preferably bound to the solid support by attachment to a second polymer molecule that is bound to the solid support.

Other preferred embodiments wherein labels are attached to the polymer further include the steps of:

(6) providing a solid support bound to a plurality of a sixth single-stranded nucleic acid sequence which is capable of hybridizing to a seventh nucleic acid sequence bonded to the first probe; and (7) providing the first probe sequence bonded both to the seventh nucleic acid sequence and to the polymer; and wherein step (4) further comprises contacting denatured target nucleic acid sequence with the solid support bonded to the sixth nucleic acid sequence.

In other preferred embodiments in which labels are attached to the polymer, the denatured target nucleic acid sequence is bound to a solid support, and step (5) involves determining the amount of label bound to the solid support. The polymer preferably is attached to an additional single-stranded nucleic acid sequence capable of hybridizing to a sixth single-stranded nucleic acid sequence, and the method further involves the steps of:

(6) providing a second labelled polymer molecule having attached a seventh single-stranded nucleic acid sequence capable of hybridizing to the sixth nucleic acid sequence; and wherein step (4) further comprises contacting the denatured target nucleic acid sequence with the second labelled polymer molecule bonded to the seventh nucleic acid sequence.

In other preferred embodiments, the first single-stranded nucleic acid sequence is a first probe sequence and, between steps (4) and (5), the complexes between the target nucleic acid sequence and the polymer molecule are trapped on a two dimensional surface, preferably a filter. The polymer molecule preferably has one or more labels attached, and step (5) involves determining the amount of label trapped on the two dimensional surface. The first probe is preferably attached to one end of the polymer molecule, which has attached at its other end a second single-stranded nucleic acid probe sequence also capable of hybridizing to the target nucleic acid sequence. When labelled polymer is employed, the DNA is preferrably double-stranded (for example, M13 DNA). When the polymer molecule is not labelled, it is preferably single-stranded DNA (for example, M13 DNA), and the method further involves the steps, between the trapping step and step (4), of contacting the denatured target nucleic acid with a single-stranded exonuclease to degrade single-stranded nucleic acids, providing a single-stranded labelled DNA capable of hybridizing to the single-stranded polymer DNA molecule, and contacting the single-stranded labelled DNA with the single-stranded polymer DNA molecule. Detection then involves determining the amount of label trapped on the two dimensional surface.

In other preferred embodiments, the first single-stranded nucleic acid sequence is a first probe sequence, the polymer molecule (preferably double-stranded DNA) is attached to a second single-stranded nucleic acid probe sequence capable of hybridizing with the target nucleic acid sequence; and the method further involves, between steps (4) and (5), forming an aqueous-polymer three dimensional network around the complexes between the target nucleic acid sequence and the polymer molecule, and removing unhybridized nucleic acid sequences from the three dimensional network, preferably by electrophoreses. The polymer molecule is preferably labelled, and step (5) involves determining the amount of label in the three dimensional network.

In other preferred embodiments where the first single-stranded nucleic acid sequence is a first probe sequence, the polymer molecule (preferably double-stranded DNA) is attached to a second single-stranded nucleic acid probe sequence capable of hybridizing with the target nucleic acid sequence; and there is formed an aqueous-polymer three dimensional network around the polymer molecule. Step (4) preferably is carried out by electrophoresing the denatured target nucleic acid sequences into the three dimensional network, and, between steps (4) and (5), the unhybridized nucleic acid sequences are removed by electrophoreses. The polymer preferably is labelled, and step (5) involves determining the amount of label in the three dimensional network.

The labels used in the methods of the invention are preferably fluorescent molecules in a concentration of $10^{-5}$ molar or less in the volume enclosed by the rms radius of the polymer molecule. The polymer molecule to which the fluorescent molecules are attached is preferably double-standard DNA.

In other preferred embodiments, the first nucleic acid sequence is a first probe sequence capable of hybridizing to the target nucleic acid sequence, and the method involves the additional steps of providing at least one additional polymer molecule bonded to a second single-stranded nucleic acid probe sequence capable of hybridizing with the target nucleic acid sequence, and, in conjunction with step (4), contacting the additional polymer molecule with the denatured target nucleic acid. Step (5) can then involve examining the mixture containing the complexes for gelation, viscosity changes, viscoelasticity changes, light scattering changes, or turbidity changes.

The advantages of the invention include: where labelled polymers are used, the amplification of detectable signal; the ability to employ large numbers of fluorescent labels while avoiding self-quenching; in some embodiments, the simple detection of hybridization without the use of labels; the provision of easy methods of separating bound from unbound label; and rapid reactions between probe and target nucleic acid sequences.

Other features and advantages of the invention will be apparent from the following description of the preferred embodiments thereof, and from the claims.

DESCRIPTION OF THE PREFERRED EMBODIMENTS

The drawings will first be described.

Drawings

FIG. 1 illustrates various conventions used in the other Figures.

FIGS. 3, 4, and 6–13 are diagrammatic representations of various embodiments of the invention.

Figure 5:
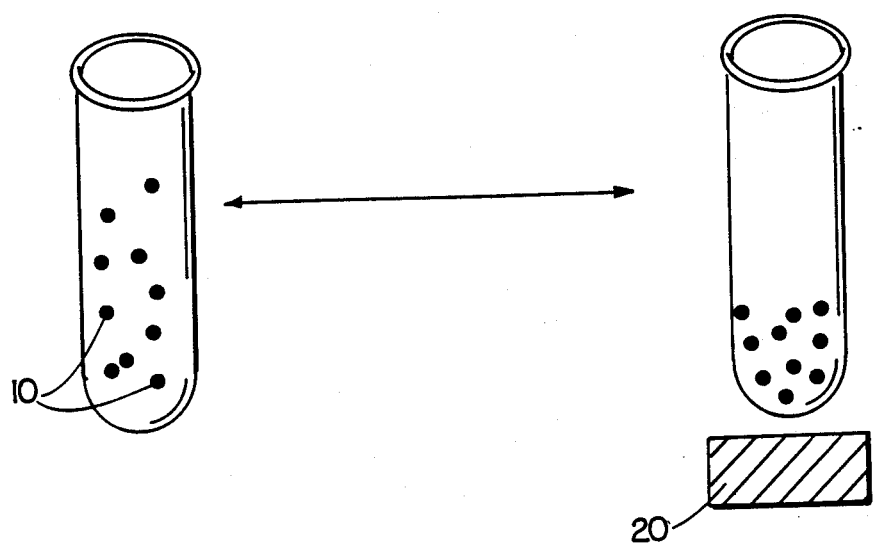

FIG. 5 is a diagrammatic representation of the measurement of viscosity using magnetic microspheres.

Components

The components of preferred embodiments are illustrated in FIG. 1. In FIG. 1(a), $P_1$ represents a single probe complementary to a target nucleic acid. In FIG. 1(b), $P_1$ and $P_2$ represent a probe pair complementary to different regions of a target nucleic acid. These different regions, although preferrably adjacent (defined herein as separated by 0–300 bases), can be located anywhere on the target sequence. In FIG. 1(c), T represents target nucleic acids. FIG. 1(d) illustrates a probe $P_1$ and probe pair $P_1$ and $P_2$ bonded to separate target sequences T. In FIG. 1(e), C is a universal sequence (defined below); also illustrated is C hybridized with its complementary universal sequence C'. Universal sequences are also represented in other Figures by the letters A, B, and D. In FIG. 1(f), L represents a label. FIG. 1(g) illustrates a random-coil polymer (defined below), and FIG. 1(h) illustrates a solid support.

Probes

Probes are single-stranded DNA or RNA molecules capable of hybridizing with target DNA or RNA.

Probes may be prepared by a variety of standard methods (e.g., Chen et al., U.S. Ser. No. 769,565, assigned to the same assignee as the present application, hereby incorporated by reference). Probes can be 16–2000 bases in length, but preferably are 20–100 bases in length, since the shorter the sequence the faster the probe will react with the target because of the reduction of excluded volume effects (discussed below).

Depending on the specificity and sensitivity requirements of the particular diagnostic test, and on the specific test configuration used, different methods of probe preparation and different combinations of probes can be utilized in the methods of the invention. For example, one or more probes can be prepared and used as follows:

a pair of probes $P_1$ and $P_2$ can be prepared as sequences complementary to different regions of a single target DNA sequence, e.g., the probes are prepared from adjacent pieces of DNA which are part of a single gene.

collections of probes can be used which represent a significant part of the whole genome of the target organism. Such "nearly-whole-genome" probes can be isolated using a combination of standard recombinant DNA and bulk isolation procedures, to yield probe collections which represent much of the genomic DNA specific for a particular microorganism but which do not hybridize to other microorganisms, to increase the sensitivity of a diagnostic test. Theoretically, a collection of 1000 such probes makes possible a diagnostic test which has a 1000-fold lower detection limit through binding 1000-fold more label at the completion of the reaction than a test where only a single-probe or probe-pair is employed.

probes can be used which are targeted against repeated DNA, messenger RNA, ribosomal RNA, or other nucleic acid sequence classes that are present in high copy-number in the target organism. Such probes are described in U.S. Pat. No. 4,302,204 (hereby incorporated by reference), where the probes hybridize to ribosomal RNA.

Universal Sequences

Universal sequences are heterogeneous base sequences which do not hybridize significantly, under test conditions, to target sequences in the test system. These sequences can be up to 200 bases in length; more preferably, they are 20 to 50 bases in length. Their value derives mainly from the fact that they are highly-repeated, low-complexity sequences. Thus, they hybridize with their complementary sequences rapidly.

Universal sequences can be obtained by standard techniques, for example, automated nucleic acid synthesis. Universal sequences are attached to probes or to DNA polymer by conventional DNA ligation methods, e.g., using DNA ligases. Depending on the requirements of a specific diagnostic test, different probe-universal sequence arrangements can be utilized. For example, a probe can have one attached universal sequence to direct labelled hybridized nucleic acids to a particular location, e.g., on a solid support; and a second attached universal sequence to enable attachment of the probe to a polymer molecule. Also, a set of different probes specific for different regions of the same targets can have the same attached universal sequence to direct labelled hybrid complexes to a single spot on a solid support; and probes specific for different targets may have attached different universal sequences to direct labelled hybrid complexes to different locations on a solid support.

Polymers

Polymers, generally random coil polymers, are used to carry probe sequences, universal sequences, and labels. Random coil polymers are chosen so that they do not readily bind to each other or to nucleic acids. Such polymers are preferably neutral or negatively charged. The polymer should be at least 50 monomer units in length, more preferably more than 1000 monomer units in length, so that each polymer molecule occupies a large hydrodynamic volume in solution.

An example of a commercially available synthetic polymer that has the above properties is linear polystyrene sulfonic acid, which has a molecular weight in the neighborhood of 6,000,000, and also advantageously has a very large hydrodynamic volume. In addition, its negative charge ensures that it will not significantly bind noncovalently to other polymer molecules or to probe or target nucleic acids. Other examples of commercially available synthetic random coil Polymers are polystyrene-maleic anhydride, neutral celluloses, polysaccharides, polydextrans, and polyamino acids (e.g., polyglutamic acid).

In addition, other useful polymers are certain biological polymers, in particular DNA and RNA. In their natural state many nucleic acid polymers are negatively charged and have very high molecular weights; for example, M13 DNA contains approximately 6,500 bases. Also, because these molecules are very stiff, particularly in double-stranded form, they take up large hydrodynamic volumes, a factor which becomes important when selecting polymers to carry fluorescent labels (discussed below). Some specific examples of random coil nucleic acid polymers are: single and double-stranded forms of M13 bacteriophage DNA; tobacco mosaic virus genomic RNA; lambda bacteriophage DNA; T2, T4, and T7 bacteriophage DNA; and pBR322 plasmid DNA. M13 DNA is of particular interest because it exists in both single and double-stranded forms and is a convenient cloning vector in *E. coli* recombinant DNA work (see Sanger et al., 74 Proc. Natl. Acad. Science, U.S.A. 5463 (1977)).

Probe and universal sequences can be bonded to the random coil polymers by standard methods. For example, methods involving covalent attachment of the sequences to polymers using known organic methods can be utilized (see Seed, 10 Nuc. Acid Res. 1799–810 (1982); Buneman et al., 10 Nuc. Acid Res. 1763–80 (1982); and U.S. Pat. No. 4,542,102, hereby incorporated by reference). For RNA or DNA polymers, in vitro biological methods involving the use of enzymes or specific nucleic acid binding proteins can be utilized (see PCT WO 85/04674 and EPC No. 0152886). In addition, in vivo biological methods whereby probe and universal sequences are bound linearly to carrier polymeric nucleic acid chains through standard restriction-ligation recombinant DNA procedures may be utilized. The in vivo recombinant DNA procedures are particularly useful because they can yield the probes or universal sequences attached to a high molecular weight cloning vector (e.g., M13 DNA). Once this polymer-nucleic acid sequence is prepared, it can be preserved and replicated in large quantity simply by growing up the host organism containing the polymer-universal or probe sequence vector.

The recombinant DNA procedures can be used to produce single-stranded or double-stranded DNA polymer molecules with probes and/or universal sequences attached at their ends. FIG. 2 illustrates several useful structures that can be obtained by these methods; for simplicity, polymer DNA molecules are represented either by single lines (single-stranded) or double lines (double-stranded). Thus, single-stranded DNA polymers can be produced with, for example, a probe $P_1$ attached (FIG. 2(*a*)(i)), a universal sequence C attached (FIG. 2(*b*)(ii)), or a probe pair $P_1$ and $P_2$ attached (FIG. 2(*b*)(iii)). Double-stranded DNA polymers can be made, for example, that have a probe $P_1$ attached (FIG. 2(*b*)(i)), two universal sequences B and C attached (FIG. 2(*b*)(ii)), or a probe pair $P_1$ and $P_2$ attached (FIG. 2(*b*)(iii)). The polymer-universal sequence structure of FIG. 2(*b*)(ii) can be reacted with a second polymer molecule that has been produced with complementary universal sequence strands B′ and C′ attached to form the larger polymer molecule illustrated in FIG. 2(*c*).

In one preferred method of obtaining a large polymer molecule with a plurality of probes $P_1$ attached, polymer DNA molecules are formed by recombinant DNA techniques with probes bonded to the ends of universal sequences; reactions between Polymer molecules having complementary universal sequences yield the larger polymer in FIG. 2(*d*)(i). The FIG. 2(*d*)(i) structure is one form of the random-coil polymer with attached Probes illustrated in FIG. 2(*d*)(ii).

It is preferable to attach the probes or universal sequences at or near their ends to the carrier polymers because, for sequences attached in such a manner, the helix-winding necessary to form double-stranded hybrids can proceed relatively unimpeded. However, it is possible to bond the sequences to the carrier polymers through nucleotides which are not at the ends of the probes or universal sequences, provided the number of attachment sites of sequence to polymer is small. Under these conditions, an adequately long double-stranded helix can form even though the winding may be interfered with or stopped after partial helix formation.

Label

In many embodiments of the invention, the polymer molecules are labelled, e.g., with a radioactive molecule or a fluorescent molecule, to allow detection of hybridization. Labelling the polymer, rather than the probe, has the advantages that many labels can be attached to each polymer molecule—thereby amplifying the signal—and that incorporating the labels into the polymer prevents the labels from interferring with the hybridization reaction.

Any of a wide variety of labels can be used. Specific examples are: radioactive labels such as P-32, S-35 and I-125; fluorescent labels such as fluorescein; and colorimetric labels such as the colored products of reactions catalyzed by enzymes such as beta-galactosidase, alkaline phosphatase, and horseradish peroxidase. Any label which can be attached to the polymer, does not interfere substantially with the hybridization reaction, and generates a detectable signal may be used.

Radioactive labels may be incorporated in DNA polymers by standard methods such as primer extension and nick translation. Fluorescent labels may be attached according to the method of Foster et al., 13 Nuc. Acids Res. 745–61 (1985).

The invention provides particular advantages where fluorescent labels are used. One problem which can occur with fluorescent labels is self-quenching of the fluorescent signal. For this reason, in fluorescent antibody detection systems, antibodies are generally labelled with only a small number of fluorescent molecules, typically on the order of 1 to 10 fluorescent groups per antibody molecule.

One of the advantages of this invention is that the large hydrodynamic volume of the high molecular-weight random-coil polymers prevents self-quenching, even when the Polymer is labelled with a large number of fluorescent groups.

The following calculation illustrates this point. Double-stranded M13 DNA has a root-mean-square (rms) radius, $<R^2>^{\frac{1}{2}}$, of approximately 2350 Å compared to a typical dimension of 100 Å for antibody molecules. The rms radius is calculated as follows from the standard formulae (see C. Tanford, Physical Chemistry of Macromolecules 150–78 (John Wiley and Sons, New York 1961).

$$<h^2>^{\frac{1}{2}} = n_k^{\frac{1}{2}} b_k$$
$$l = n_k b_k$$
$$<R^2>^{\frac{1}{2}} = \frac{<h^2>^{\frac{1}{2}}}{\sqrt{6}}$$

In these formulae, $l$ is the contour length of the random coil polymer, $b_k$ is the Kuhn length (the length of a random segment), $n_k$ is the number of Kuhn units (the number of random segments), and $<h^2>^{\frac{1}{2}}$ is the rms end to end distance of the random coil polymer.

Based on 6500 base pairs in M13 DNA and 3.4 Å per base Pair, the contour length is $6500 \times 3.4 = 2.2 \times 10^4$ Å. For double-stranded DNA in typical solutions, the Kuhn length is approximately 1500 Å (D. Lang, 54 Molecular Biol. 557 (1970)). Substitution into equations (1) through (3) gives the 2350 Å value for M13 double-stranded DNA.

This rms radius of M13, a measure of the extension of the M13 DNA in space or hydrodynamic volume, is about 23 times that of a typical antibody. Therefore, fluorescent labels attached randomly to M13 DNA will be, on the average, much farther apart than the same number of labels attached to a typical antibody molecule, and therefore will exhibit significantly less self-quenching.

To complete this illustrative calculation, it is well known that in typical aqueous solutions fluorescein begins to show self-quenching around $10^{-5}$ molar, and very high self-quenching occurs at $10^{-4}$ molar. (see K. Schauenstein et al., 26 J. Histochem. & Cytochem. 277–83 (1978)). For 100 fluorescein molecules contained in the volume enclosed by the rms radius of M13, the fluorescein concentration is calculated:

$$\text{concentration} = \frac{100/6.023 \times 10^{23}}{(4/3 \pi) \times (2.35 \times 10^{-5})^3 \times 10^{-3}} = 3.1 \times 10^{-6} \text{ molar}$$

This fluorescein concentration is significantly less than that for which self-quenching will occur. Thus, the calculation shows that one M13 double-stranded DNA molecule can bind many more than 100 fluorescein groups without significant self-quenching. Therefore, very large random-coil polymers such as DNA are excellent carriers for fluorescent labels. For other fluorescein carrying polymers a similar calculation can be made using the above equation if the Kuhn length and polymer and monomer molecular weights are known.

Solid Support

Standard solid supports, e.g., filters, coated latex beads, and coated magnetic beads, can be used in some embodiments of the invention. Probe sequences, universal sequences, and target nucleic acids can be attached to the solid support by known standard techniques, either directly or via a polymer attached to the solid support by standard techniques.

Assays

In hybridizations where probe or target DNA is bound to a solid support directly by the usual procedures, it is wellknown that much of the bound DNA is unavailable for hybridization with complementary DNA. This is most likely because: (1) each DNA molecule is usually bound to the solid support at several sites, thereby restricting the helix-winding necessary to form double-stranded nucleic acid hybrids; (2) there are steric or excluded volume effects due to the physical bulk of the filter, due to DNA molecules lying on top of one another, and due to negatively-charged bound DNA's in close proximity to each other on the two-dimensional filter surface.

The components described above may be utilized in a variety of ways that minimize the above-mentioned effects, and that facilitate user-friendly diagnostic kits. Different embodiments will require different user steps, and may produce different organism detection limits or specificities. Thus, for a particular diagnostic or detection application, one particular embodiment may be more appropriate than another.

There are three general approaches to designing the diagnostic tests of the invention: homogeneous assays, heterogeneous assays, and combinations of the two. In a homogeneous assay, hybridization of a probe to its target and detection of hybridization both take place in solution, and are thus accomplished without separation of hybridized and unhybridized nucleic acids. In a heterogeneous assay, hybridization of a probe to its target takes place on a solid support, so that hybridized and unhybridized nucleic acids are physically separated to allow detection. In the combination assay, the hybridization reaction occurs in solution (i.e., in homogeneous phase), but detection of hybridization occurs either through a subsequent attachment of hybridized molecules to the solid support via universal nucleic acid sequences, or through a subsequent concentration or entrapment of the hybridized nucleic acids by other means.

In homogeneous assays, the hybridization of the probes and the target nucleic acid takes place in solution. The problems associated with filter hybridization are thus avoided, and hybridization occurs at an optimal rate.

In addition, because the high molecular weight random-coil polymer used occupies a large hydrodynamic volume, cross-linking two or more molecules of the polymer through the target sequence can increase the viscosity and viscoelasticity of the solution. Under some circumstances, when sufficient cross-links are formed, detectable gelation can occur. These phenomena can be detected by various user-friendly means, including, in some cases, means which do not require labels such as radioactive isotopes.

The different properties of extensively cross-linked networks compared to linear or branched random-coil polymers offer unique ways of separating them from the polymer-bound sequences which have not reacted with target DNA, as will be described in detail below.

The use of polymers offers advantages in heterogeneous assays as well, e.g., signal amplification provided by the plurality of labels on each polymer molecule.

Polymers bound to a solid support can also be advantageously utilized in heterogeneous designs. For example, by utilizing a sandwich assay protocol where the manufacturer binds polymer-bound probes to a solid support, the intensity of the signal from the label can be further greatly increased by restricting the polymer-bound probe to a very small area on the support (intensity=amount of signal/area). In addition, where the probes are end-bound to the polymer, helix-winding problems and steric effects can be reduced. If the polymer is a random-coil polymer, the polymer and probes extend into three-dimensional space, thereby making them more available for reaction with target nucleic acid. While there will be some steric effects associated with the bulk of the random-coil, these effects should be minimal since the space occupied by random-coils is generally more than 95% solvent.

The mixed assays offer advantages associated with both the homogeneous and heterogeneous methods. The hybridization of the probe to the target nucleic acid takes place in solution and thus hybridization occurs at a much faster rate. The hybridized product is then either bonded to or trapped in a heterogeneous manner, so detection is straightforward.

There are described below a number of particular embodiments of the invention. While they include a wide range of methods and kits, the practitioner skilled in the art of diagnostic kit design will be able to devise other similar methods and kits utilizing the concepts of the invention.

A. Homogeneous Reaction and Detection Methods

Two assay designs are discussed, followed by a description of the various detection techniques that can be utilized with both.

EXAMPLE 1

Figure 3:
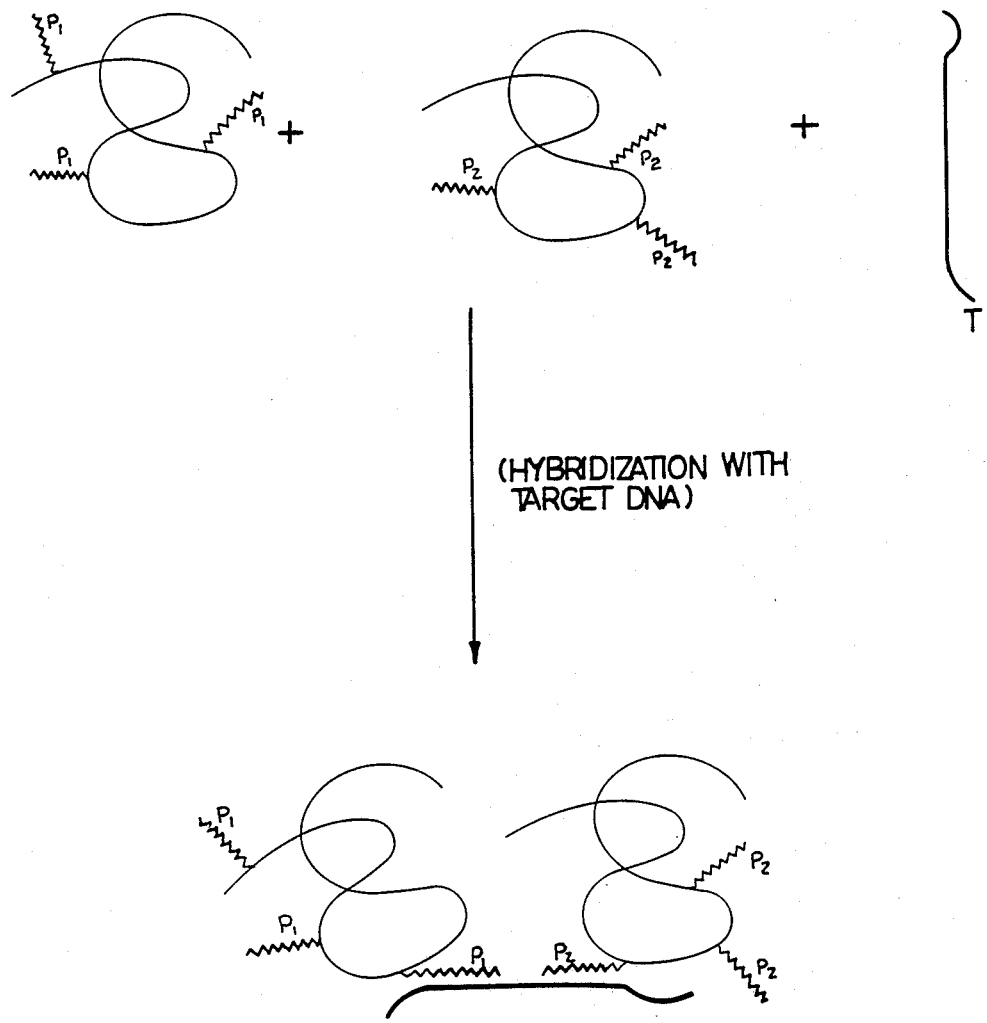
Figure 4A:
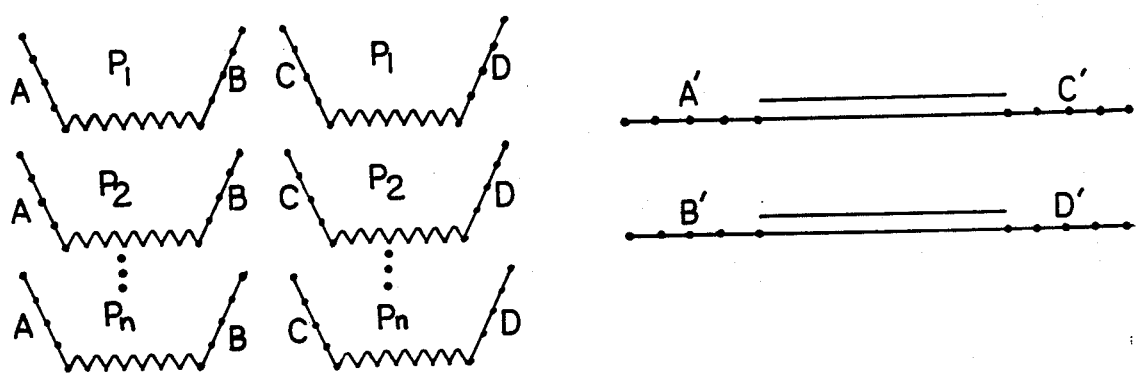
Figure 4B:
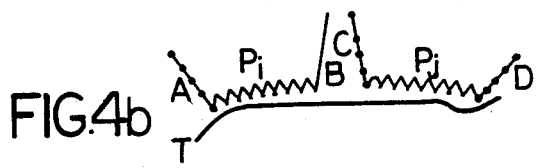
Figure 4B:
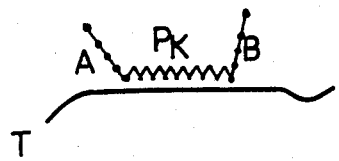
Figure 4C:
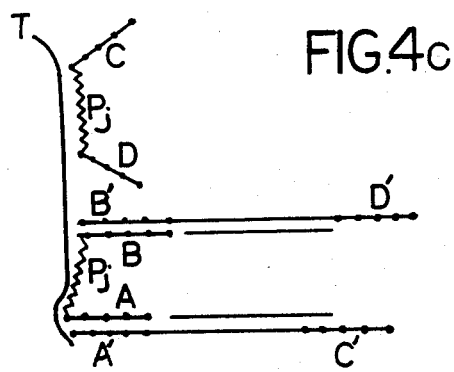

Referring to FIG. 3, probes $P_1$ and $P_2$ are homologous to different adjacent regions of target nucleic acid sequence T and are attached to random-coil polymers. Successful hybridization of probes to target results in cross-linking of the polymers. Extensive cross-linking can result in the formation of a gel; for less extensive cross-linking, significant changes in viscosity and other measurable hydrodynamic properties will occur.

Since in the cross-linking methods it is often desirable to form as large a number of crosslinks as possible, nearly-whole genome probes are preferred. Another excellent way to form extensive crosslinking is to select probes against ribosomal RNA, high copy number messenger RNA, and repeated DNA.

EXAMPLE 2

FIG. 4 illustrates another homogeneous assay design. A probe collection $P_1, P_2, \ldots P_n$ are specific for the target nucleic acid T. To the probe collection are attached universal sequences A, B, C, and D, homologous to universal sequences A', B', C', and D' that are attached to the ends (or at other positions) of a large, random-coil polymer (e.g., double-stranded DNA (FIG. 4(a)). The first step is to hybridize T to the probe collection (FIG. 4(b)). The unhybridized probes are then physically separated from the hybridized nucleic acids; the separation can be simply accomplished by filtering or other straightforward physical means, since T is much larger than the unreacted probes. Typically, for example, T is prepared by cell lysis and alkali denaturation and will contain over 50,000 bases, whereas the probes plus the universal sequences will contain generally no more than about 300 bases.

After separation of the unreacted material, the reacted probe-target complex is reacted with the universal sequence-containing DNA. To keep the illustration simple, only two DNA's are shown crosslinked in FIG. 4(c). Clearly, many DNA's can be readily crosslinked in this fashion as each target will have many bound probes attached, and each DNA has two sites for crosslinking. Thus, large crosslinked networks are built up, and if sufficient crosslinking occurs, viscosity or other detectable changes will occur (see below), and in some cases a gel will form.

In this example, the requirement for a measurably high viscosity or gelation means that many crosslinks must form and each crosslinked species must have a very high molecular weight. Thus, for detection of bacteria, typically $10^{10}$ target sequences are required, when the crosslinking molecules are 5-times the hydrodynamic radius of a single M13 molecule. Accordingly, a mass of $10^5$ bacteria each having $10^4$ ribosomal genes could be detected when contacted with 10 specific probes under suitable conditions for hybridization. Thus, while this embodiment provides for very user-friendly detection, it is of practical use mainly in cases where the number of target sequences is quite large. This high target sequence requirement can be met, for example, by using probes against ribosomal RNA of bacteria.

The Example 2 embodiment has a subtle advantage over that described in Example 1 in that the kinetics will be considerably faster because of a significant reduction in excluded volume. Excluded volume effects on hybridization rate occur because the bulk and negative charge of the two reacting nucleic acid molecules makes less available some of the bases for the first step (nucleation) in helix formation. The rate constant, k, for hybridization of two complementary single-strands of lengths L and M bases is given by $$k = K'x\,(1/L^{0.55} + 1/M^{0.55})$$

In this equation, K' takes into account complexity and all other factors of the renaturation reaction. (See Hinnebusch, Clark, and Klotz, 17 Biochem. 1521 (1978) for a discussion of excluded volume effects on renaturation rate in nucleic acid hybridizations.)

The equation shows that as the number of bases of the strands increases, the reaction is correspondingly slower. For example, a 10-fold increase in the length of both L and M would result in a 3.5-fold decrease in rate constant. This rate reduction can be particularly problematic for reactions involving target DNA, since this DNA generally contains many bases, is generally present in very small amounts, and reacts very slowly.

If one of the reacting strands remains small, according to the equation, the rate constant will remain approximately the same no matter how large the complementary strand becomes. In Example 2, the probe-universal sequence strand is small, typically a few hundred bases at most.

The reactions of the universal linker DNAs, A, B, C, D with their complementary partners, A', B', C', D', will be fast despite excluded volume, because they are present in much higher concentration than any particular target DNA sequence.

Detection

An advantage of all the homogeneous methods is the ease of detection of hybridization. Since the physical properties of extensively crosslinked polymers are very different from the non-crosslinked polymers, user-friendly detection methods utilizing no attached label are possible. Under conditions where very extensive crosslinking takes place so that a gel forms, the gelation can be detected by several methods. For example, touching the surface of the gelled solution could be sufficient to detect gelation; alternatively, gelation can be detected in a capillary tube containing the gel, since a gel has infinite viscosity, so it will not flow in a capillary.

Even where crosslinking is not extensive enough for gelation to occur, which would be the usual case, the networks formed will exhibit significant changes in viscosity and/or viscoelasticity (for a discussion of viscoelasticity of large DNA, see L. C. Klotz and B. H. Zimm, 72 J. Med. Bio. 779-800 (1972)). Viscosity changes can be detected by any one of many well-known traditional methods (e.g., capillary viscometers, concentric cylinder viscometers, large falling spheres). For a discussion of viscosity measurements, see K. E. Van Holde, Physical Biochemistry 154-56 (Prentice-Hall 1971). In addition to the traditional methods, novel, more user-friendly methods can be used to detect viscosity. For example, the rate or amount of movement of large numbers of magnetic microspheres in a magnetic field can be used to detect a viscosity increase due to polymer networking. FIG. 5 illustrates the magnetic microsphere procedure. The sample to be analyzed is placed in a tube, along with suspended, colloidol magnetic microspheres 10. After the hybridization and cross-linking reactions are carried out, the tube is placed over magnet 20, which draws the spheres toward the bottom of the tube. By comparing the rate of downward movement of the spheres in the sample to that in a control (unhybridized) sample, the degree of viscosity change can be detected. If desired, the magnetic microspheres can be colored or fluorescently labelled to make detection with the naked eye or by instruments easier.

A further method of detecting crosslinking is by measuring changes in light scattering or turbidity in the solution containing the hybridized nucleic acids. The light scattering techniques are particularly well adapted to large DNA polymers such as double-stranded M13 DNA. As a rule of thumb, molecules with an rms radius greater than 1/20 the wavelength of light will scatter enough light for practical detection. A linear double-stranded M13 DNA has an rms radius of approximately 2350 Å. Visible light ranges between 4000-7000 Å wavelength. Thus, even collections of single M13 DNA molecules will scatter significant light, and networks of these molecules will scatter considerably more light. By comparing the light scattered in the sample to that contained in the control, the level of crosslinking can be detected. For a discussion of light scattering of solutions of polymer molecules, see C. Tanford, Physical Chemistry of Macromolecules, 275-315 (John Wiley & Sons 1961). The same general principles apply to turbidity measurements.

B. Heterogeneous Reaction and Detection Methods

Three examples are presented in this section. In the Figures, only one probe or probe pair is shown. Preferably, more than one probe or probe pair is used; the probes illustrated are meant to be representative of a group of probes.

EXAMPLE 1

Figure 6:
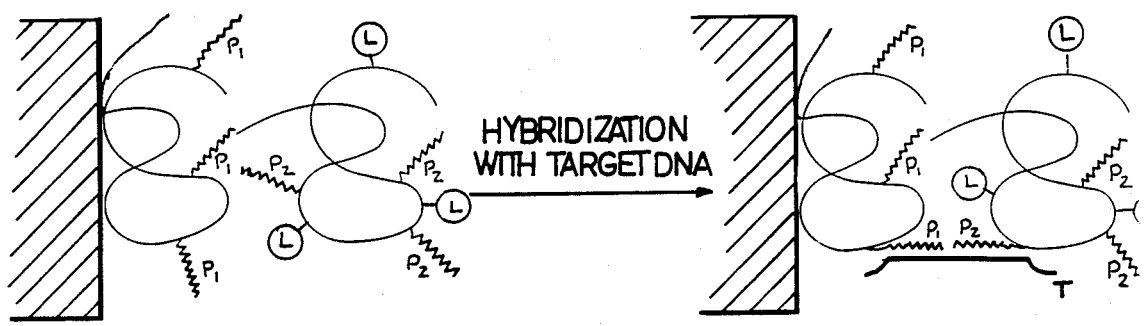

FIG. 6 illustrates an example of a heterogeneous-type assay. Probe $P_1$, homologous to a region of target nucleic acid sequence, is attached to a polymer that in turn is attached to a solid support. Probe $P_2$, homologous to a different but adjacent region of T, is attached to a labelled polymer. Single-stranded T, $P_1$, and $P_2$ are mixed together. $P_1$ hybridizes to T, causing the target to be bonded to the solid support; $P_2$ also hybridizes to T, resulting in the labelled polymer being bonded to the solid support through T. The two hybridization reactions can, of course, occur in the opposite order. Hybridization of probes to target is detected by the amount of label bound to the solid support.

EXAMPLE 2

Figure 7:
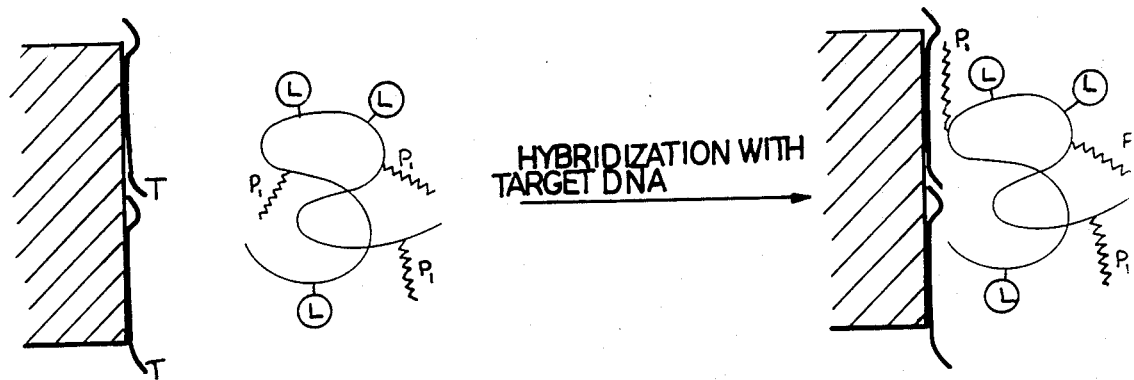

FIG. 7 illustrates another heterogeneous-type assay design. Denatured target nucleic acid sequence T is bonded to the filter by standard methods. Probe $P_1$, homologous to a region of T and attached to a labelled polymer, is contacted with T to allow hybridization. Upon successful hybridization, the labelled polymer will be bound to the solid support and, as in Example 1, hybridization is detected by the amount of label bound to the solid support.

Figure 2A:
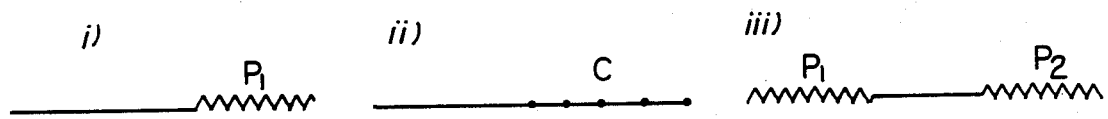
FIG. 2 illustrates some representative probe-polymer configurations of the invention.
Figure 2B:
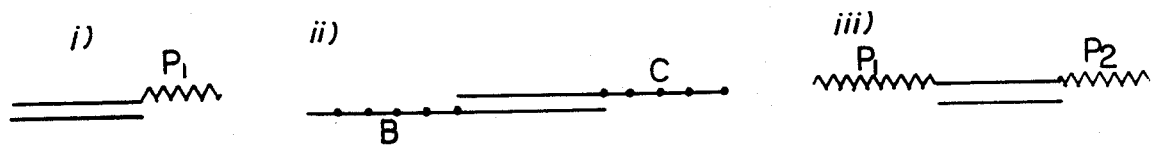
Figure 2C:
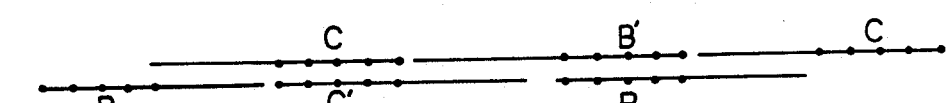
Figure 2D:
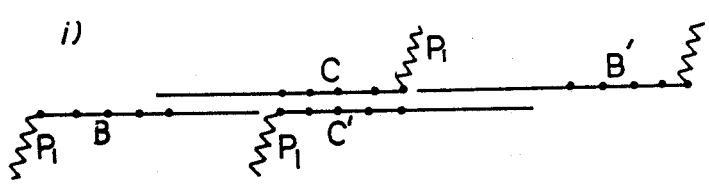

In both Examples 1 and 2, detection is facilitated by the amplification of the signal associated with each T. For example, one double-stranded DNA molecule can carry 100 fluorescent labels without significant self-quenching. Furthermore, several DNA molecules can be linked together through universal DNA sequences (as illustrated in FIG. 2(c)), and therefore each linked polymer molecule can have 500 to several thousand labels associated with it. If the fluorescent labelled M13 polymer is selected to carry $P_1$ in Example 2 (or $P_2$ in Example 1), after hybridization is complete, 1000 fluorescent labels are bonded to hybridized T (which, in turn, is bonded to the solid support); the signal associated with a T molecule, therefore, is greatly amplified.

EXAMPLE 3

Figure 8:
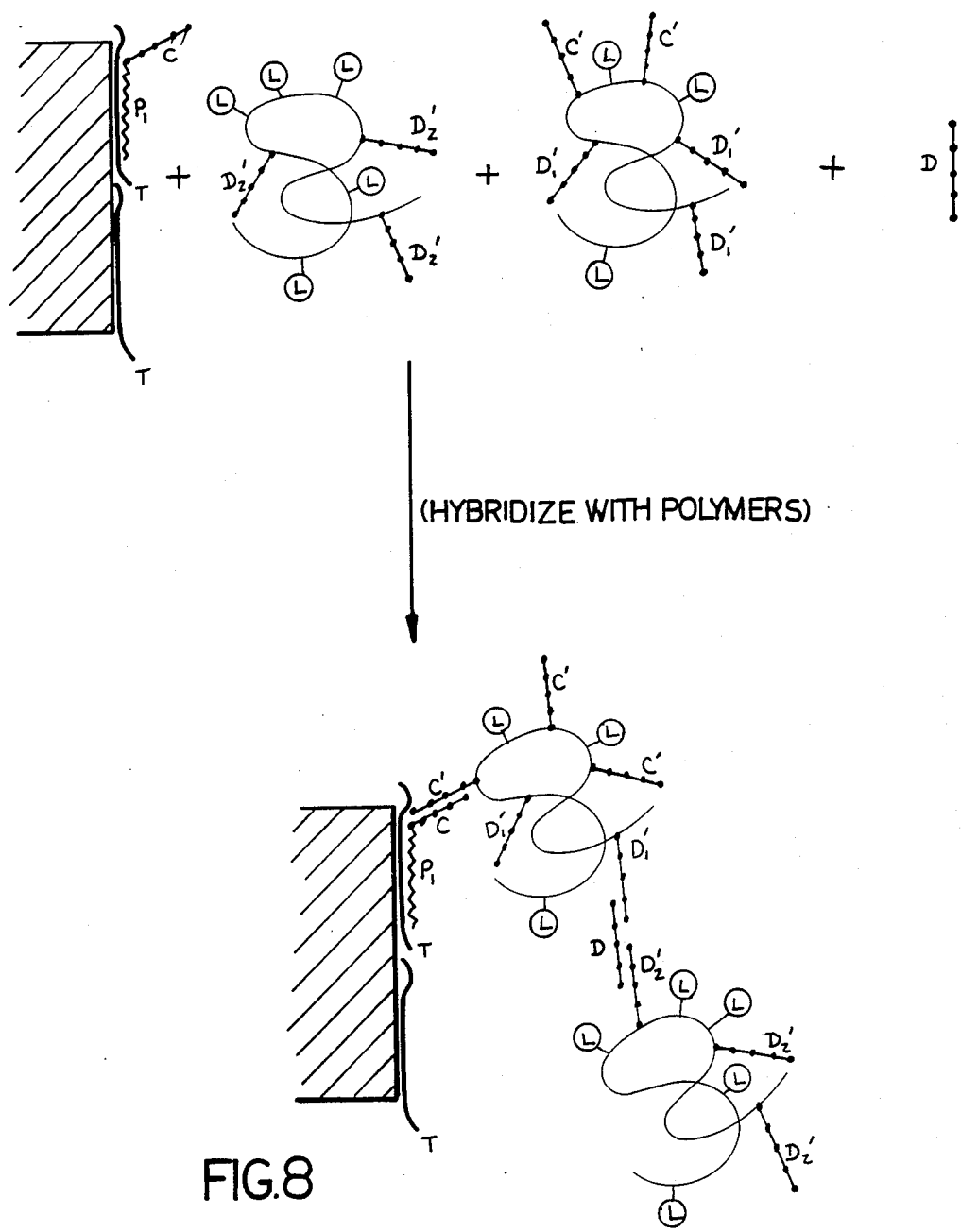

Referring to FIG. 8, the amount of label bonded to each target nucleic acid sequence T is increased greatly through cross-linked networks. As in Example 2, denatured T is bonded to a solid support. Each probe $P_1$, homologous to a region of T, has attached a universal sequence C homologous to a universal sequence (C') that is attached to a labelled polymer. The labelled polymer also has attached universal sequence $D'_1$. $P_1$ is contacted with T, and, following hybridization of $P_1$ to T, the labelled polymer carrying C' is contacted with the solid support, allowing hybridization of C' to C. A second polymer molecule carrying universal sequence $D'_2$ is then added, along with cross-linking universal sequence D, which contains sequences homologous to both $D'_1$ and $D'_2$, and which, following hybridization of the homologous sequences, serves as a cross-linker between the two polymer molecules. Large networks of labelled polymer can thus be built up around each T, making for more sensitive detection than in Examples 1 and 2. As in Examples 1 and 2, hybridization is detected by the amount of label bound to the solid support.

C. Assay Designs Utilizing Homogeneous Reaction and Heterogeneous Detection Methods

EXAMPLE 1

Figure 9:
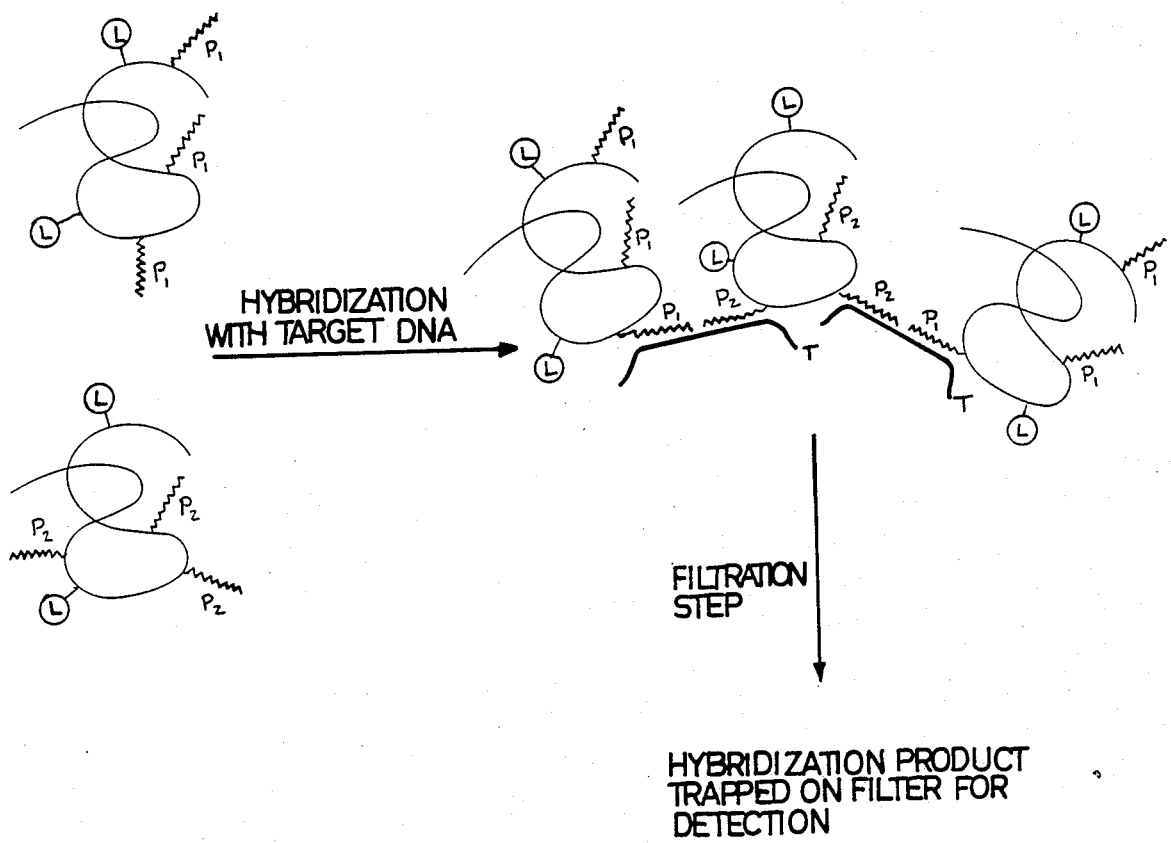

FIG. 9 illustrates an assay in which a hybridization reaction has occurred between denatured target nucleic acid sequence T and probes $P_1$ and $P_2$, each of which is attached to a labelled polymer, preferably a double-stranded DNA, such as M13 DNA. It is preferred that many probes homologous to different portions of T be used in the assay to maximize the number of polymers in each cross-linked complex; $P_1$ and $P_2$ are meant to be representative of that group. After the hybridization reaction is complete, the reacted material can be trapped on a two-dimensional surface (e.g., a filter) for detection of hybrids; filters may be selected from the many commercially available whose separation characteristics are such that single polymer molecules will pass through the filter, but the crosslinked networks will not.

Fluorescent groups or other labels can be readily detected on the filter. With respect to fluorescent labels, as previously discussed, double-stranded M13 can be provided as a 10-unit linked segment, and each of the units can carry up to 100 fluorescein labels with minimal self-quenching.

EXAMPLE 2

Figure 10:
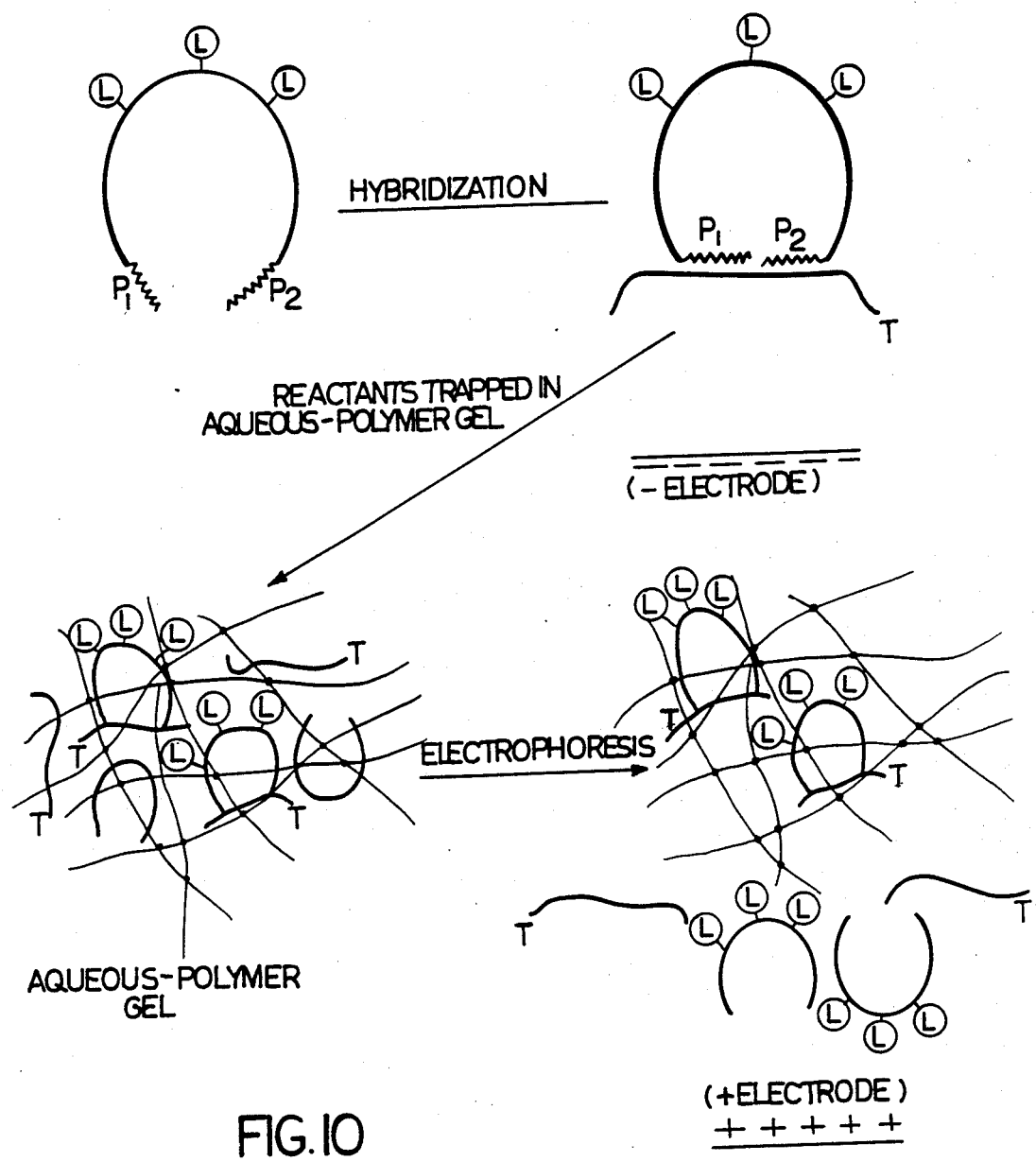

Circular nucleic acids can be separated from linear nucleic acids by a number of techniques. FIG. 10 illustrates an assay design based on the differences between circular and linear DNA.

In FIG. 10, the target nucleic acid sequence T reacts with single-stranded probes $P_1$ and $P_2$, which are attached to opposite ends of a labelled, linear DNA molecule such as M13. The probes are complementary to adjacent segments of the target DNA, and the reaction with T converts the linear DNA into a circular form. If an aqueous polymer three-dimensional network is formed in the solution after the hybridization reaction takes place, the rings will become trapped in the network as illustrated in FIG. 10. Because of this entrapment, the rings can be separated from the linears in several ways. For example, the linear, non-hybridized DNA can be electrophoresed away from the entrapped rings because the entrapped rings are immobile in the electric field.

The ring-closure embodiment offers kinetic advantages over standard sandwich assays. Due to the close proximity of the two probe-carrying ends of the rings, once the target DNA has reacted with the probe on one end, the reaction with the probe on the other end can often be faster than with probe in free solution.

Several types of networks can be used for trapping depending on the size of the rings. For example, for small rings, acrylamide gels or commercially available networks of glass fibres may be used. For larger rings, larger pore networks of glass fibres or other porous filters may be used.

EXAMPLE 3

Figure 11:
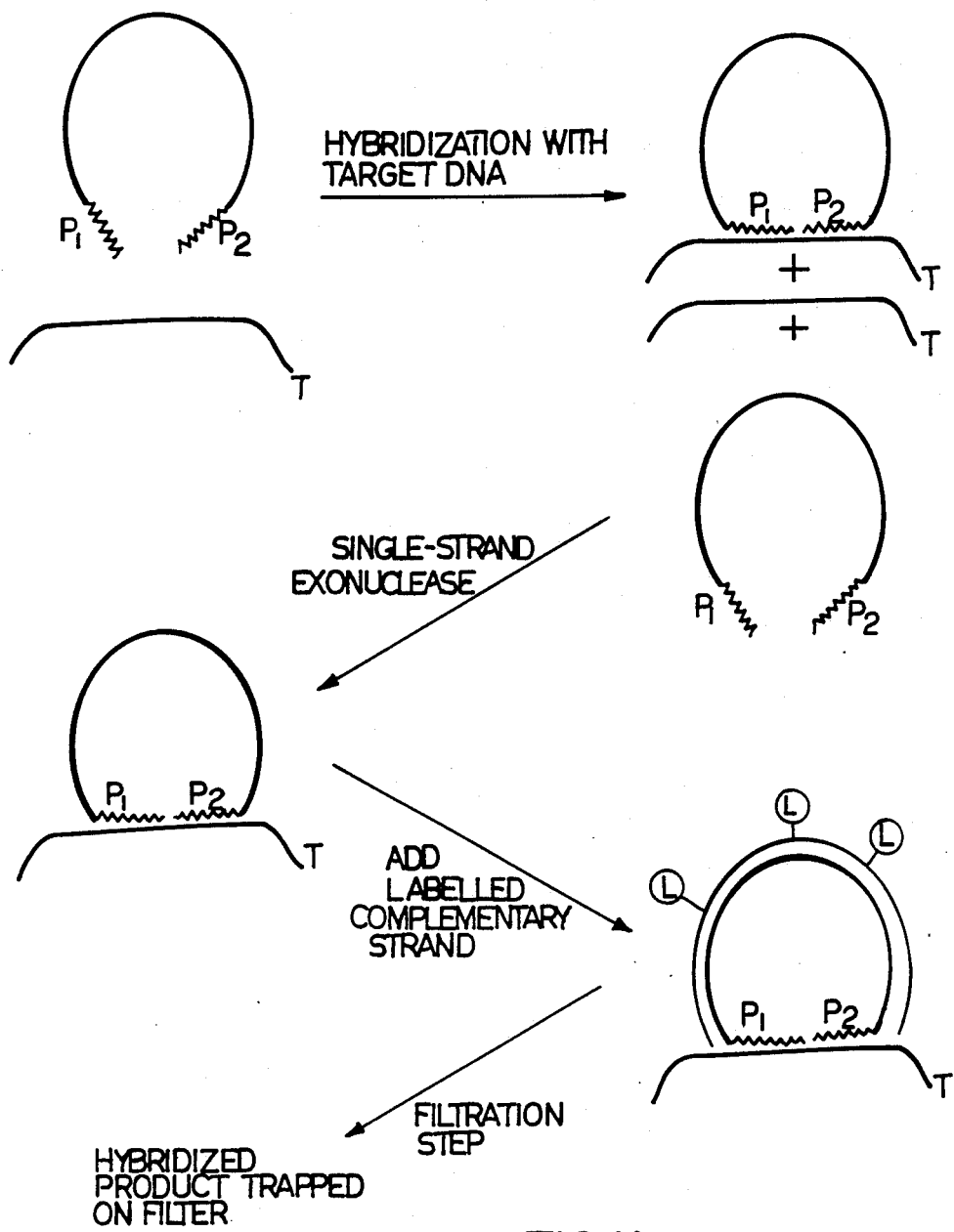

FIG. 11 illustrates another assay design that takes advantage of the different properties of linear and circular nucleic acids; in this case, their different reactivities with enzymes. In one embodiment, a low molecular weight single-stranded DNA is prepared with probes $P_1$ and $P_2$ on each end. The two probes are complementary to adjacent segments of target nucleic acid sequence T. When the probes hybridize with T, the circle closes, eliminating the single-strand ends. A single-strand exonuclease, such as exonuclease VII from *E. coli*, is added to the reaction mixture to degrade any remaining single-stranded DNA with exposed ends, i.e., the remaining unreacted single-stranded, linear DNA. After degradation is complete, the remaining circular DNA is reacted with complementary, labelled DNA, and the reaction product trapped on a small diameter filter for detection.

The Example 3 design has the advantage that probe-polymer DNA which has not reacted with target DNA is totally degraded to nucleotides and is thereby quite easily separated from reacted DNA by any of a number of means, including filtration, electrophoresis, exclusion chromatography, and ethanol precipitation.

EXAMPLE 4

Figure 12:
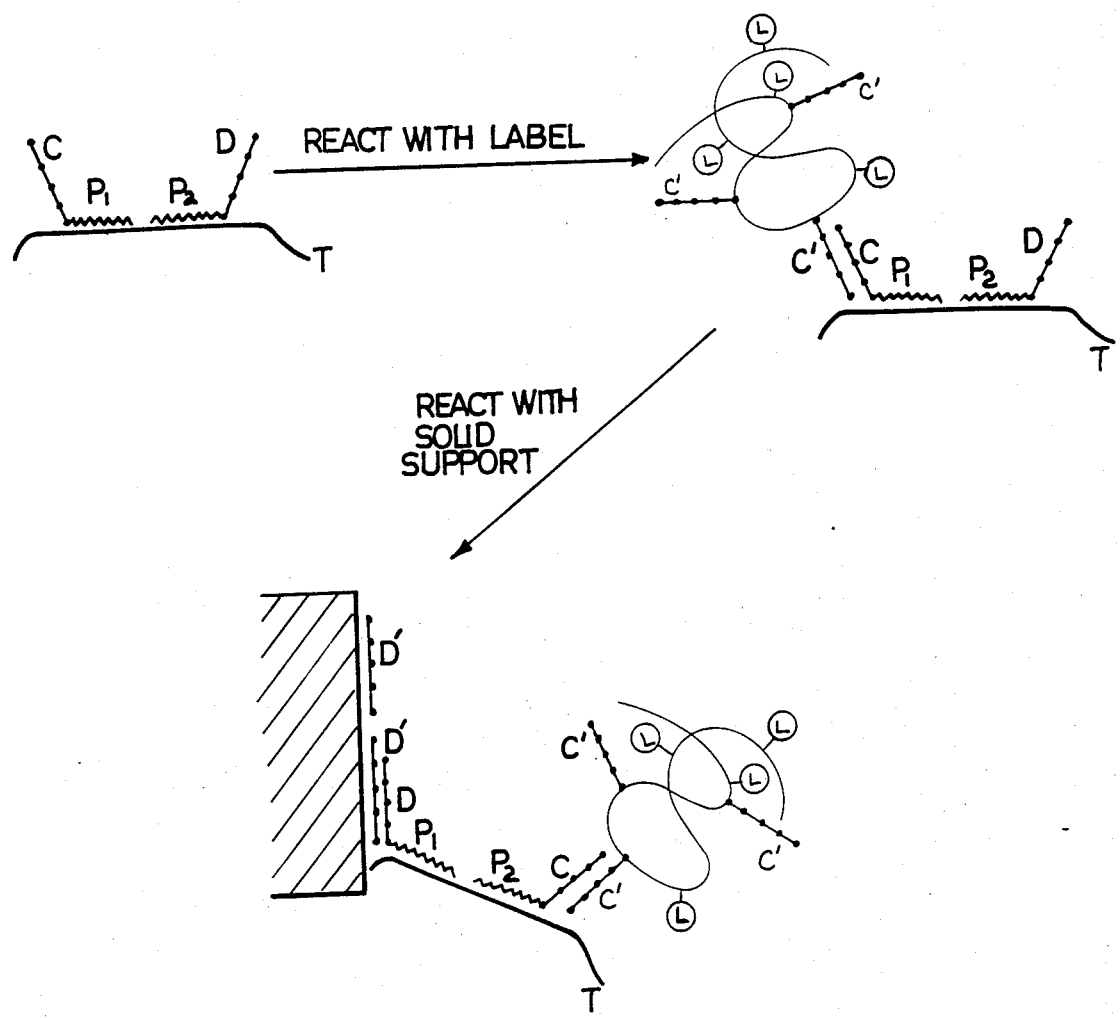

FIG. 12 illustrates an assay design that utilizes universal sequences. The probe pairs, $P_1$, $P_2$, etc., are attached to universal sequences C and D as illustrated. Each probe pair represents probes prepared to be complementary to adjacent sequences on the target DNA.

The probes are reacted with target nucleic acid sequence T in solution and under conditions where excluded volume effects are minimized. Following the reaction, the universal sequences are utilized both to label reacted T and to direct T to the appropriate spots on the solid support. Homologous universal sequences C' attached to the polymer bring about the labelling of the probe-target when the universal sequences hybridize.

Universal nucleic acid sequence D' attached to the solid support directs the probe-target to a particular spot on the support; detection is facilitated because a high concentration of labelled target nucleic acid collects on the solid support as a result of the hybridization between homologous universal sequences D and D'. The problems associated with filter hybridiztion are minimized in this case for two reasons. First, universal nucleic acid sequences can be loaded onto the filter in high concentration, providing more sequences for the homologous sequence of the probe to hybridize with. Second, because the universal sequences are of low complexity (short length) the hybridization will occur at a faster rate (see Britten et al., 161 Science 529 (1968) for a discussion of the increased reaction speed when the binding sites are highly concentrated, low complexity nucleic acid sequences).

Besides the advantages of this method already mentioned, there are other potential advantages. Different D and D' pairs can be utilized on probes specific for different organisms. Thus several different organisms can be detected simultaneously in a single test in the same solution since the different D, D' complementary pairs will direct the labels to different locations on the solid support.

The sensitivity theoretically obtainable utilizing this method is quite good. Pandex, Inc., has shown that $6 \times 10^6$ fluorescein molecules can be detected on a planar 2 mm diameter area (see Jolly et al., 67 J. Immun. Methods 21-35 (1984)). In the Example 4 design, the manufacturer can bind the D. sequences to 2mm spots precisely located, so that many tests can be carried out simultaneously by the user with no incremental user effort. Furthermore, where, e.g., M13 DNA is used as the polymer, each M13 molecule carries 1000 labels, and as few as 6000 target sequences complementary to the probes can be detected. If nearly-whole-genome probes are utilized, fewer than 100 organisms can be detected. Such low detection limits are more than adequate for detection of the microorganisms involved, e.g., in periodontal disease and for bacteriuria testing, without the need for colony growth.

EXAMPLE 6

Figure 13:
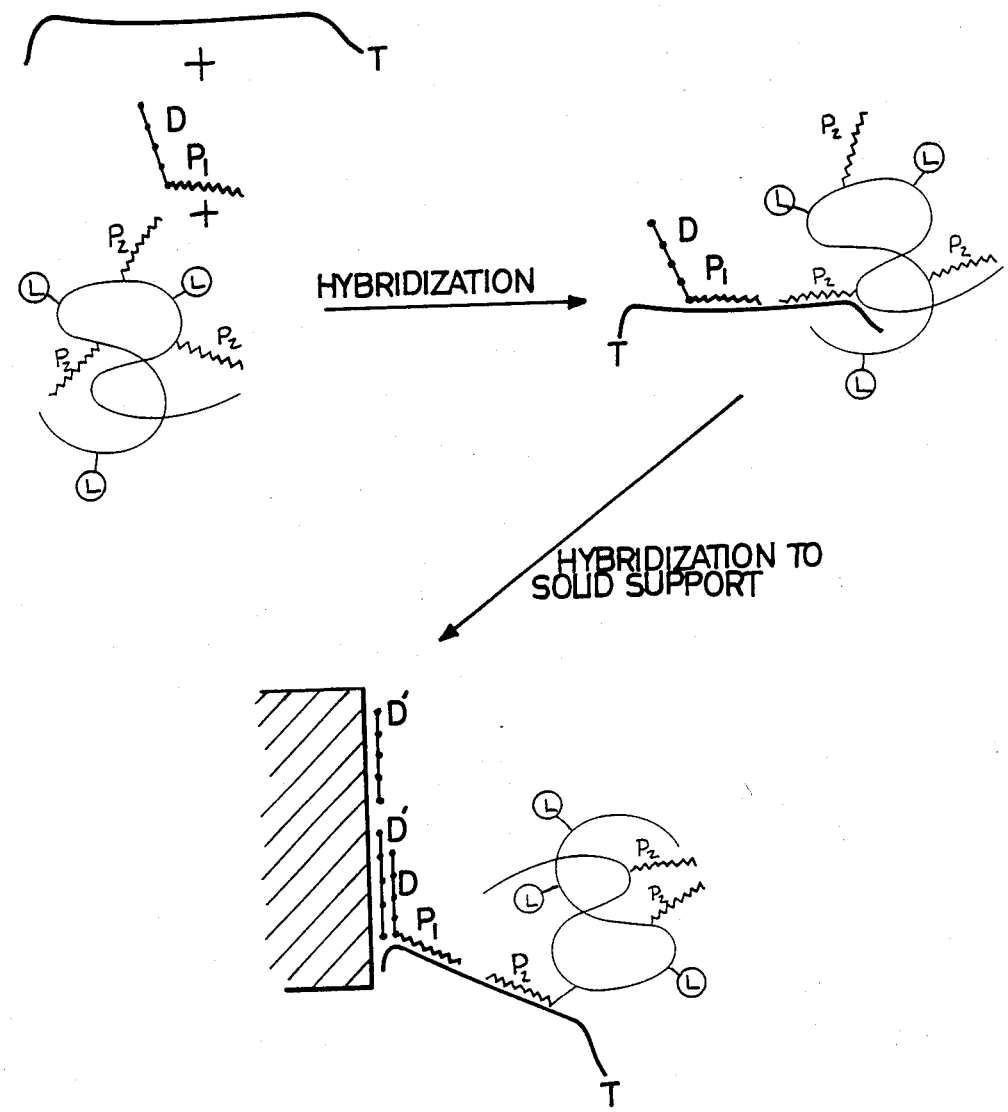

FIG. 13 also illustrates an assay design that utilizes universal sequences. Probe $P_1$ is attached to universal sequence D, which is homologous to universal sequence D' on the solid support. Probe $P_2$ is attached to a labelled polymer. $P_1$ and $P_2$, are contacted with target nucleic acid T. Following hybridization, the solid support is added to the mixture. Hybridization of D. and D binds labelled T to the solid support for detection.

Other embodiments are within the following claims.

We claim:

1. A method for carrying out a nucleic acid hybridization test to detect a target nucleic acid sequence, said method comprising the steps of
   (1) providing a polymer molecule bonded to a first single stranded nucleic acid sequence comprising a first probe which hybridizes to a first target nucleic acid sequence when present, provided that, where said polymer molecule comprises DNA, said DNA is of heterogeneous base sequence;
   (2) denaturing said target nucleic acid sequence;
   (3) contacting said denatured target nucleic acid sequence with said polymer molecule bonded to said first single stranded nucleic acid sequence;
   (4) separating out complexes between said target nucleic acid sequence and said polymer molecule by trapping said complexes on a two-dimensional surface; and
   (5) detecting complexes between said target nucleic acid sequence and said polymer molecule;
   wherein said polymer molecule is attached to a second single-stranded nucleic acid probe sequence which hybridizes to said target nucleic acid sequence when present; and
   wherein the region of said target nucleic acid sequence to which said first probe hybridizes is adjacent to the region of said target nucleic acid sequence to which said second probe hybridizes.

2. The method of claim 1, wherein said polymer molecule is single-stranded DNA.

3. The method of claim 2, further comprising the step, between said trapping step and step (5), of contacting said denatured target nucleic acid with a single stranded exonuclease to degrade single-stranded nucleic acids.

4. The method of claim 3, further comprising the steps, between said contacting steps and said trapping step, of:
   providing a single-stranded labelled DNA molecule capable of hybridizing with said single-stranded polymer DNA molecule; and
   contacting said single-stranded labelled DNA with said single-stranded polymer DNA molecule.

5. The method of claim 4, wherein said step (5) comprises determining the amount of label trapped on said two-dimensional surface.

6. The method of claim 5, wherein said two-dimensional surface is a filter.

7. The method of claim 6, wherein said single stranded polymer DNA molecule is M13 DNA.

8. The method of claim 6, wherein said first probe sequence and said second probe sequence are attached at opposite ends of said single-stranded polymer DNA molecule.

9. The method of claim 1, wherein said polymer molecule is double-stranded DNA.

10. The method of claim 9, wherein said polymer molecule is labelled.

11. The method of claim 10, wherein said step (5) comprises determining the amount of label trapped on said two-dimensional surface.

12. The method of claim 11, wherein said two-dimensional surface is a filter.

13. The method of claim 12, wherein said double-stranded polymer DNA molecule is M13 DNA.

14. The method of claim 12, wherein said first probe sequence and said second probe sequence are attached at opposite ends of said double-stranded polymer DNA molecule.

15. A method for carrying out a nucleic acid hybridization test to detect a target nucleic acid sequence, said method comprising the steps of:
   (1) providing a polymer molecule bonded to a first single-stranded nucleic acid sequence comprising a first probe which hybridizes to said target nucleic acid sequence when present, provided that, where said polymer molecule comprises DNA, said DNA is of heterogeneous base sequence;
   (2) denaturing said target nucleic acid sequence;
   (3) contacting said denatured target nucleic acid sequence with said polymer molecule bonded to said first single stranded nucleic acid sequence; and
   (4) detecting complexes between said target nucleic acid sequence and said polymer molecule;
   wherein said polymer molecule is attached to a second single-stranded nucleic acid probe sequence which hybridizes with said target nucleic acid sequence when present; and
   wherein the region of said target nucleic acid sequence to which said first probe which hybridizes is adjacent to the region of said target nucleic acid sequence to which said second probe hybridizes.

16. The method of claim 15, further comprising the step, between said steps (4) and (5), of forming an aqueous-polymer three dimensional network around said complexes of said target nucleic acid sequence and said polymer molecule.

17. The method of claim 16, further comprising the step, between said forming step and said step (5), of removing unhybridized said first probe sequences, second probe sequences, and unhybrodized said target nucleic acid sequences from said three dimensional network.

18. The method of claim 17, wherein said removing step is carried out by electrophoresis.

19. The method of claim 18, wherein said polymer molecule is DNA.

20. The method of claim 19, wherein said DNA is double-stranded M13 DNA.

21. The method of claim 20, wherein said polymer molecule is labelled.

22. The method of claim 21, wherein said step (5) comprises determining the amount of said label in said three dimensional network.

23. The method of claim 15, further comprising the step, prior to said step (4), of forming an aqueous-polymer three dimensional network around said polymer molecule.

24. The method of claim 23, wherein said step (4) is carried out by electophorexing said denatured target nucleic acid sequences into said three dimensional network.

25. The method of claim 24, further comprising the additional step, between said steps (4) and (5), of removing unhybridized said first nucleic acid sequences, unhybridized said target nucleic acid sequences from said three dimensional network.

26. The method of claim 25, wherein said removing step is performed by electrophoresis.

27. The method of claim 26, wherein said polymer molecule is DNA.

28. The method of claim 27, wherein said DNA is double-stranded M13 DNA.

29. A method for carrying out a nucleic acid hybridization test to detect a target nucleic acid sequence, said method comprising the steps of
  (1) providing a polymer molecule bonded to a first single-stranded nucleic acid sequence comprising a first probe which hybridizes to said target nucleic acid sequence when present, provided that, where said polymer molecule comprises DNA, said DNA is of heterogeneous base sequence;
  (2) denaturing said target nucleic acid sequence;
  (3) contacting said denatured target nucleic acid sequence with said polymer molecule bonded to said first single stranded nucleic acid sequence;
  (4) detecting complexes between said target nucleic acid sequence and said polymer molecule; and
  (5) providing at least one additional polymer molecule, each said additional polymer molecule being attached to a second single-stranded nucleic acid probe sequence which hybridizes with said target nucleic acid sequence when present;
    wherein step (3) further comprises contacting said additional polymer molecule with said denatured target nucleic acid sequence; and
    wherein said step (4) comprises determining whether gelation of the mixture containing said complexes has occurred.

30. A method for carrying out a nucleic acid hybridization test to detect a target nucleic acid sequence, said method comprising the steps of
  (1) providing a polymer molecule bonded to a first single stranded nucleic acid sequence comprising a first probe which hybridizes to said target nucleic acid sequence when present, provided that, where said polymer molecule comprises DNA, said DNA is of heterogeneous base sequence;
  (2) denaturing said target nucleic acid sequence;
  (3) contacting said denatured target nucleic acid sequence with said polymer molecule bonded to said first single-stranded nucleic acid sequence;
  (4) detecting complexes between said target nucleic acid sequence and said polymer molecule; and
  (5) providing at least one additional polymer molecule, each said additional polymer molecule being attached to a second single-stranded nucleic acid probe sequence which hybridizes with said target nucleic acid sequence when present;
    wherein step (3) further comprises contacting said additional polymer molecule with said denatured target nucleic acid sequence; and
    wherein said step (4) comprises determining changes in light scattering of the mixture containing said complexes.

31. A method for carrying out a nucleic acid hybridization test to detect a target nucleic acid sequence, said method comprising the steps of
  (1) providing a polymer molecule bonded to a first single-stranded nucleic acid sequence comprising a first probe which hybridizes to said target nucleic acid sequence when present, provide that, where said polymer molecule comprises DNA, said DNA is of heterogeneous base sequence;
  (2) denaturing said target nucleic acid sequence;
  (3) contacting said denatured target nucleic acid sequence with said polymer molecule bonded to said first single-stranded nucleic acid sequence;
  (4) detecting complexes between said target nucleic acid sequence and said polymer molecule; and
  (5) providing at least one additional polymer molecule, each said additional polymer molecule being attached to a second single-stranded nucleic acid probe sequence which hybridizes with said target nucleic acid sequence when present;
    wherein step (3) further comprises contacting said additional polymer molecule with said denatured target nucleic acid sequence; and
    wherein said step (4) comprises determining changes in turbidity of the mixture containing said complexes.

32. A method for carrying out a nucleic acid hybridization test to detect a target nucleic acid sequence, said method comprising the steps of
  (1) providing a polymer molecule bonded to a first single-stranded nucleic acid sequence comprising a second nucleic acid sequence which hybridizes to a third nucleic acid sequence, when present, bonded to a first probe which hybridizes to said target nucleic acid sequence when present, provided that, where said polymer molecule comprises DNA, said DNA is of heterogeneous base sequence;
  (2) denaturing said target nucleic acid sequence;
  (3) contacting said denatured target nucleic acid sequence with said polymer molecule bonded to said first single-stranded nucleic acid sequence;
  (4) detecting complexes between said target nucleic acid sequence and said polymer molecule;
    wherein a plurality of said polymer molecules are provided; and
    wherein said step (4) comprises determining whether gelation of the mixture containing said complexes has occured.

33. A method for carrying out a nucleic acid hybridization test to detect a target nucleic acid sequence, said method comprising the steps of
  (1) providing a polymer molecule bonded to a first single-stranded nucleic acid sequence comprising a second nucleic acid sequence which hybridizes to a third nucleic acid sequence, when present, bonded to a first probe which hybridizes to said target nucleic acid sequence when present, provided that, where said polymer molecule comprises DNA, said DNA is of heterogeneous base sequence;
  (2) denaturing said target nucleic acid sequence;
  (3) contacting said denatured target nucleic acid sequence with said polymer molecule bonded to said first single-stranded nucleic acid sequence;
  (4) detecting complexes between said target nucleic acid sequence and said polymer molecule;

wherein a plurality of said polymer molecules are provided; and wherein said step (4) comprises determining changes in light scattering of the mixture containing said complexes.

34. A method for carrying out a nucleic acid hybridization test to detect a target nucleic acid sequence, said method comprising the steps of (1) providing a polymer molecule bonded to a first single-stranded nucleic acid sequence comprising a second nucleic acid sequence which hybridizes to a third nucleic acid sequence, when present, bonded to a first probe which hybridizes to said target nucleic acid sequence when present, provided that, where said polymer molecule comprises DNA, said DNA is of heterogeneous base sequence;

(2) denaturing said target nucleic acid sequence;

(3) contacting said denatured target nucleic acid sequence with said polymer molecule bonded to said first single-stranded nucleic acid sequence;

(4) detecting complexes between said target nucleic acid sequence and said polymer molecule;

wherein a plurality of said polymer molecules are provided; and wherein said step (4) comprises determining changes in turbidity of the mixture containing said complexes.

35. The method of claim 3, wherein said exonuclease is exonuclease VII or *E. coli*.

* * * * *

UNITED STATES PATENT AND TRADEMARK OFFICE
CERTIFICATE OF CORRECTION

PATENT NO. : 4,925,785

DATED : May 15, 1990

INVENTOR(S) : Chang-Ning J. Wang et al.

It is certified that error appears in the above-identified patent and that said Letters Patent is hereby corrected as shown below:

Column 19, line 10, insert --second nucleic acid probe sequences, and unhybridized said-- before "target".

Signed and Sealed this

Thirty-first Day of December, 1991

Attest:

HARRY F. MANBECK, JR.

Attesting Officer      Commissioner of Patents and Trademarks

UNITED STATES PATENT AND TRADEMARK OFFICE
CERTIFICATE OF CORRECTION

PATENT NO. : 4,925,785

DATED : May 15, 1990

INVENTOR(S) : Chang-Ning J. Wang et al.

It is certified that error appears in the above-identified patent and that said Letters Patent is hereby corrected as shown below:

On the title page, item [56] References Cited:
Under "Foreign Patent Documents" add "8504674 10/1985 Blakesley et al".

Column 19, line 10, insert --second nucleic acid probe sequences, and unhybridized said-- before "target".

Signed and Sealed this

Sixth Day of July, 1993

MICHAEL K. KIRK

Attest:

Attesting Officer

Acting Commissioner of Patents and Trademarks